(12) United States Patent
Ludescher et al.

(10) Patent No.: US 7,847,093 B2
(45) Date of Patent: Dec. 7, 2010

(54) PROCESSES FOR THE PREPARATIONS OF CEFEPIME

(75) Inventors: Johannes Ludescher, Breitenbach (AT); Hubert Sturm, Innsbruck (AT); Siegfried Wolf, Brixlegg (AT)

(73) Assignee: Sandoz AG, Basel (CH)

( * ) Notice: Subject to any disclaimer, the term of this patent is extended or adjusted under 35 U.S.C. 154(b) by 624 days.

(21) Appl. No.: 10/552,858

(22) PCT Filed: Apr. 15, 2004

(86) PCT No.: PCT/EP2004/003988
§ 371 (c)(1), (2), (4) Date: Oct. 12, 2005

(87) PCT Pub. No.: WO2004/092183
PCT Pub. Date: Oct. 28, 2004

(65) Prior Publication Data
US 2007/0105830 A1 May 10, 2007

(30) Foreign Application Priority Data
Apr. 16, 2003 (AT) .................. A 584/2003
Apr. 16, 2003 (AT) .................. A 585/2003
Apr. 16, 2003 (AT) .................. A 586/2003

(51) Int. Cl.
*C07D 501/46* (2006.01)
*C07D 501/40* (2006.01)
(52) U.S. Cl. ................................... 540/222
(58) Field of Classification Search ............... None
See application file for complete search history.

(56) References Cited

U.S. PATENT DOCUMENTS

| | | | |
|---|---|---|---|
| 4,266,049 A | 5/1981 | Bonjouklian | |
| 4,336,253 A | 6/1982 | Lunn et al. | |
| 4,406,889 A | 9/1983 | Hartmann et al. | |
| 4,489,072 A | 12/1984 | Imaizumi et al. | |
| 4,692,516 A | 9/1987 | Kirrstetter et al. | |
| 4,767,852 A | 8/1988 | Ascher | |
| 4,959,495 A | 9/1990 | Curran et al. | |
| 4,960,766 A | 10/1990 | Takaya et al. | |
| 5,026,843 A | 6/1991 | Riccardo et al. | |
| 5,109,131 A | 4/1992 | Naito et al. | |
| 5,574,154 A | 11/1996 | Abu-Nasrieh | |
| 5,574,155 A | 11/1996 | Danklmaier et al. | |
| 5,583,216 A | 12/1996 | Ochiai et al. | |
| 6,384,215 B1 | 5/2002 | Deshpande | |
| 6,458,949 B1 | 10/2002 | Handa et al. | |
| 6,919,449 B2* | 7/2005 | Deshpande et al. | 540/222 |
| 7,339,055 B2* | 3/2008 | Deshpande et al. | 540/215 |
| 7,479,556 B2* | 1/2009 | Manca et al. | 540/222 |
| 2002/0156272 A1 | 10/2002 | Totschnig et al. | |
| 2005/0043531 A1* | 2/2005 | Handa et al. | 540/224 |
| 2005/0080070 A1* | 4/2005 | Deshpande et al. | 514/202 |
| 2006/0058281 A1* | 3/2006 | Senthilkumar et al. | 514/203 |
| 2006/0094872 A1* | 5/2006 | Senthilkumar et al. | 540/217 |
| 2006/0100424 A1* | 5/2006 | Manca et al. | 540/200 |

FOREIGN PATENT DOCUMENTS

| | | |
|---|---|---|
| EP | 0030294 | 6/1981 |
| EP | 0074268 | 3/1983 |
| EP | 0 137 440 | 4/1985 |
| EP | 0335297 | 10/1989 |
| EP | 0492277 | 7/1992 |
| EP | 0 531 981 | 3/1993 |
| EP | 0842937 | 11/1996 |
| WO | WO 00/63214 | 10/2000 |
| WO | WO 2006067803 A1 * | 6/2006 |

OTHER PUBLICATIONS

Database Casreact XP002297198; Database Accession No. 140:111151 RX(1) and Gong et al., Hongguo Yaowu Huaxue Zazhi, vol. 12, No. 6, pp. 350-351, 362 (2002).
Walker, "New Cephalosporin Acylating Agents Derived from SYN-2(2-Aminothiazol-4-YL)-2-Methoxyimino Acetic Acid. Application to the Synthesis of Cefepime Sulfate", Tetrahedron Letters, vol. 31, No. 45, pp. 6481-6484 (1990).
Donald G. Walker, et al., "Use of Bistrimethylsilylated Intermediates in the Preparation of Semisynthetic 7-Amino-3-substituted-cephems. Expedient Syntheses of a new 3-[(1-Methyl-1-pyrrolidinio)methyl] cephalosporin," 1988 American Chemical Society, J. Org. Chem, 1988, 53, pp. 983-991.
J. E. Swigor, et al.,"Synthesis of 7-[alpha-(2-aminothiazol-4-yl)-alpha-(z)-methoximinoacetamido]-3-(1-[14C] methylpyrrolidinio)-methyl-3-cephem-4-carboxylate Sulfate," Journal of Labelled Compounds and Radiopharmaceuticals—vol. XXIV, No. 1, pp. 15-22.
Tomoyasu Ishikawa, et. al., "Synthesis and Antibacterial Activity of 7Beta-[2-(5-Amino-1,2,4-thiadiazol-3-yl)-2(Z)-alkoxyiminoacetamido]-3-(substituted limidazo[1,2-b]pyridazinium-1-yl)methyl-3-cephem-4-carboxylates and Related Compounds," The Journal of Antibiotics, vol. 53, No. 10, Oct. 2000, pp. 1071-1085.

(Continued)

*Primary Examiner*—Mark L Berch
(74) *Attorney, Agent, or Firm*—Luedeka, Neely & Graham, P.C.

(57) ABSTRACT

This invention provides processes for preparing cefepime, including crystalline intermediates of Formula V.

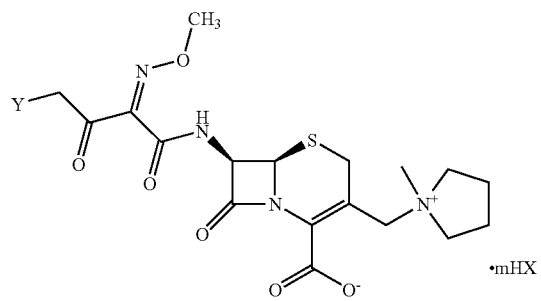

(V)

7 Claims, 2 Drawing Sheets

OTHER PUBLICATIONS

Mitsuo Numata, et al., "New Cephalosporins with 7-Acyl Groups Derived from Beta-Katoacids," The Journal of Antibiotics, Dec. 1978, pp. 1252-1261.

Mitsuo Numata, et al., "A New Cephalosporin. SCE-963: 7-[2-(2-Aminothiazo-4-YL)-acetamido]-3-[[[1-(2-Dimethylaminothyl)-1H-Tetrazol-5-YL]-Thio]Methyl]Ceph-3-EM-4-Carboxylic Acid," The Journal of Antibiotics, Dec. 1978, pp. 1262-1271.

Hideaki Yamanaka, et al., "Studies of Beta-Lactam Antibiotics IX. Synthesis and Biological Activity of a New Orally Active Cephalosporin, Cefixime (FK027)," The Journal of Antibiotics, Dec. 1985, pp. 1738-1751.

* cited by examiner

PROCESSES FOR THE PREPARATIONS OF CEFEPIME

This application claims priority to PCT Application Serial Number PCT/EP04/003988 to Ludescher et al. filed on Apr. 15, 2004, entitled PROCESSES FOR THE PREPARATIONS OF CEFEPI which further claims priority to (1) Austrian Patent Application Serial Number 584/2003 filed on Apr. 16, 2003, (2) Austrian Patent Application Serial Number 585/2003 filed on Apr 16, 2003, and (3) Austrian Patent Application Serial Number 586/2003 filed on Apr. 16, 2003, the contents of all of which are incorporated herein by reference in their respective entireties.

The present invention relates to the preparation of 1-[[(6R,7R)-7-[[(2Z)-(2-amino-4-thiazolyl)methoxyimino)acetyl]amino]-2-carboxy-8-oxo-5-thia-1-azabicyclo[4.2.0]oct-2-en-3-yl]methyl]-1-methyl-pyrrolidinium dihydrochloride hydrate (cefepime dihydrochloride monohydrate), hereafter "cefepime". Cefepime is a valuable 4th generation injectable cephalosporin with antibacterial properties, see e.g. The Merck Index Thirteenth Edition, Item 1935, and is used e.g. in the form of a dihydrochloride hydrate of formula I

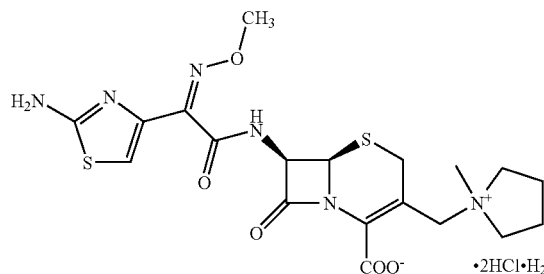

I

Presently known methods for preparing cefepime are far from straightforward. For example, it is known that the 7-acyl side chain as the difficultly obtainable 2-(2-aminothiazol-4-yl)-2-methoxyimino-acetic acid chloride hydrochloride must be used for the production of cefepime, in order to obtain an active ingredient which is pure in respect of the by-products known as anti-isomer and Δ-2 isomer.

The present applicants have sought to overcome the problems of hitherto known processes.

In one aspect, therefore, this invention provides a process comprising reaction of a β-lactam intermediate of formula IIA or IIB

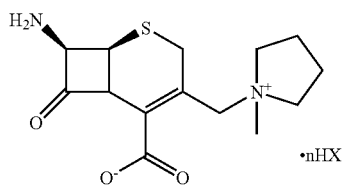

II A

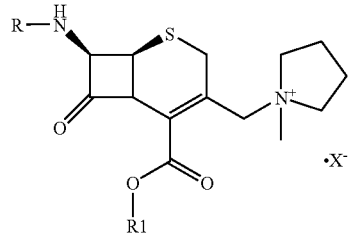

II B wherein
$R_1$ is trialkylsilyl,
R is H or trialkylsilyl
n is 0-2 and
X is chloride, bromide or iodide,
with a reactive derivative of the compound of formula III

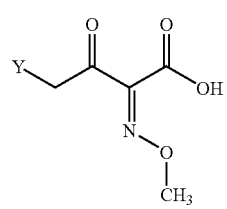

III wherein Y is halogen or a leaving group, to form a compound of formula IV or V

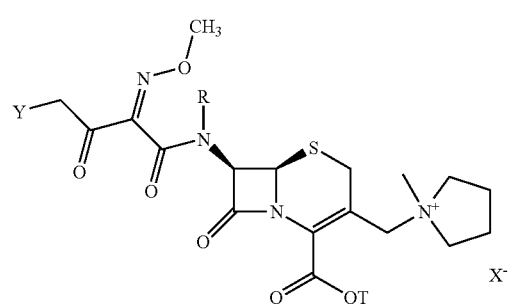

IV wherein T is trialkylsilyl, the silyl protecting groups—if present—are removed, if necessary the intermediate step of formula V

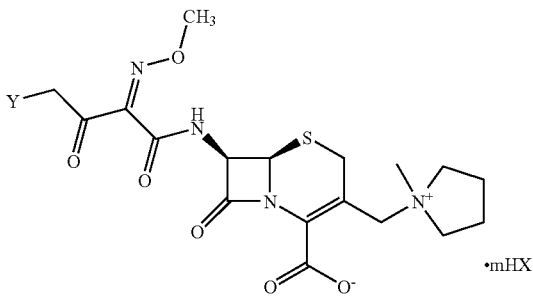

V is isolated wherein m is 0 or 1, the compound of formula IV, or the compound of formula V, is reacted with thiourea and subsequently the compound of formula I is isolated.

Examples of trialkylsilyl protecting groups are trimethylsilyl and triethylsilyl.

When Y represents halogen, Y may denote chloride, bromide or iodide, preferably chloride or bromide. Leaving group is understood in the context of this invention to denote a group which is removed by reaction with e.g. thiourea, e.g. alkyl or aryl sulfonyl, e.g. $C_1$-$C_4$ alkyl sulfonyl.

Unless otherwise stated, alkyl means $C_1$-$C_8$ alkyl, e.g. $C_1$-$C_4$ alkyl, e.g. methyl, ethyl, propyl or butyl and may be straight or branched chain.

Unless otherwise stated, the compounds of formula IIA and IIB are referred to as compounds of formula II.

It will be appreciated that the compounds of formula II or V may exist in mixtures. Thus the compound of formula IIA may exist in a mixture having a proportion where n is 1, and a proportion where n is 2. The compound of formula IIB may exist in a mixture comprising mono- and di-silylated forms.

The compounds of formula II may be used in free base form, as a mono-addition salt or as a di-addition salt with a hydrohalic acid such as hydrochloric acid, hydrobromic acid or hydriodic acid. The addition salts may additionally be present in solvated form, e.g. as a hydrate.

If the silylation variant is chosen, the intermediate of formula IIB is obtained by known methods, using a silylation agent such as N,O-bis-(trimethylsilyl)-acetamide (BSA), N,O-bis-(trimethylsilyl)-trifluoroacetamide (BSTFA), N-methyl-N-trimethylsilyl-trifluoroacetamide (MSTFA) or for example hexamethyldisilazane (HMDS), in a solvent that is inert towards silylation agents, for example a nitrile, such as acetonitrile, an ether, for example tetrahydrofuran, or a chlorinated hydrocarbon, for example dichloromethane.

Subsequently, the silylated derivative of formula IIB is acylated with a reactive derivative of formula III, the reactive derivative being an acid chloride, acid bromide or active ester, for example a S-mercaptobenzothiazolyl ester, optionally in the presence of an auxiliary base such as a tertiary alkylamine.

The compound of formula IV is subsequently desilylated with the assistance of a protic reagent, for example water or an alcohol, and then the compound of formula V is reacted with thiourea in an aqueous or organic-aqueous medium. Cefepime is subsequently crystallised, if necessary after separating the organic solvent, and where appropriate after removing any salt that is present, for example after treatment using anion exchangers by known methods after adding hydrochloric acid from an aqueous acetonic solution.

An alternative is to work in an aqueous or aqueous-organic system, for example in a one-phase system consisting of water and a water-miscible solvent, for example a ketone, such as acetone, a nitrile, such as acetonitrile, or an ether, such as tetrahydrofuran, or in a two-phase system, for example in a combination of an ester of acetic acid, for example ethyl acetate, a chlorinated hydrocarbon, for example dichloromethane, or for example an aromatic hydrocarbon, for example toluene, whereby the compound of formula IIA is optionally released from its respective mono- or di-addition salt form with the assistance of a base, for example caustic soda solution or caustic potash solution, a sodium or potassium hydrogen carbonate or alkali carbonate, or by known methods using an ion exchanger, and subsequently the compounds of formula II are acylated with a reactive derivative of formula III. After the acylation reaction has taken place, thiourea is added, and after optionally separating the organic solvent, the title compound is isolated by known methods by adding acetone from an aqueous/acetonic solution.

Suitable ion exchangers include ion exchange resins comprising e.g. LA2 which is available commercially from the Rohm and Haas company.

If desired, it is possible to isolate the compound of formula V, at this stage as an addition salt with a hydrohalic acid, for example as the hydrochloride, or isolate as free base. Here, the reaction sequence preferably starts with an acid addition salt of the compound of formula I, via the silylation route. By adding small amounts of protic solvent, for example water or an alcohol, to the compound of formula IV, the silyl groups are removed, and the halide present in the system enables direct crystallisation of the compound of formula V to take place. The preferred mono-addition salt is the monohydrochloride in crystalline form. In order to produce this, the compound of formula IIA is preferably used as the mono- or di-hydrochloride addition salt, and the preferred solvents for crystallisation are acetonitrile in combination with isopropanol.

To isolate the compound of formula V as free base in crystalline form, the above procedure may be used with addition of a suitable base to the solution or suspension of the acid addition salt of the compound of formula V. Alternatively, the acid addition salt of the compound of formula V may be isolated and subsequently converted to the corresponding free base by addition of a suitable base. Suitable bases include for example trialkylamines, e.g. triethylamine for example in an alcoholic solvent such as methanol.

In U.S. Pat. No. 4,266,049, a 7-acyl-3-acetoxymethyl-cephalosporinate is converted with the assistance of an iodotrialkylsilane into the corresponding persilylated 3-iodomethyl compound and this then undergoes nucleophilic substitution in the 3'-position. This technology can only be applied to the production of cefepime—starting with cefotaxime—to an uneconomical extent, since N-methylpyrrolidine as a strong base can greatly induce the formation of the by-products Δ-2 und und 7-epi (Walker et al, J. Org Chem. 1988, pages 983-991).

The present applicants found that working with N-methylpyrrolidine—trialkylsilane adducts iodotrimethylsilane and N-methylpyrrolidine as described in the above literature led to unsatisfactory results when using cefotaxime as the starting material.

In another aspect therefore, this invention provides a synthesis route from cefotaxime (see Merck Index, $12^{th}$ Edition, item 1983) in accordance with the following scheme:

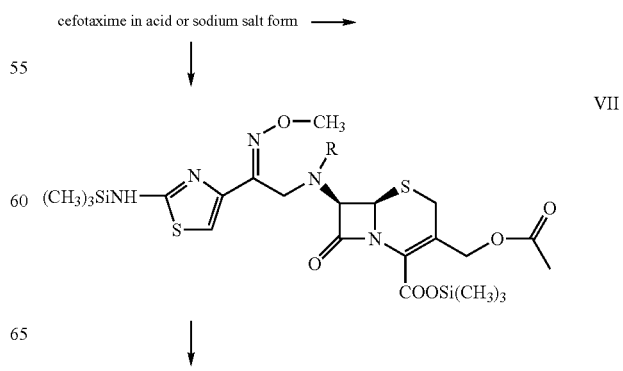

-continued

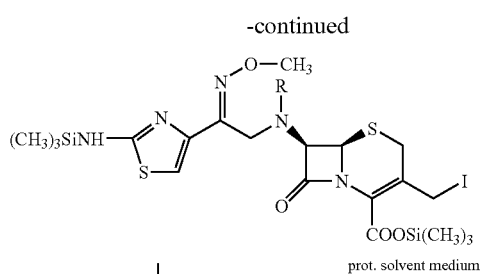

VIII prot. solvent medium

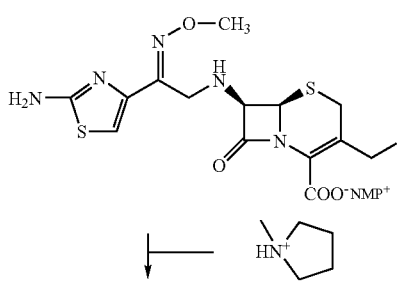

IX

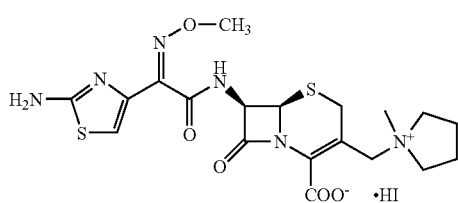

X

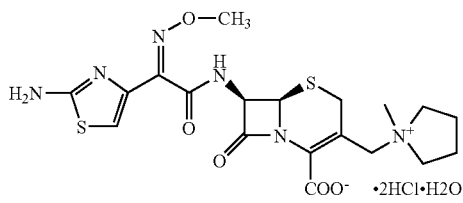

I

The choice of silylation agent is crucial to the smooth conversion of cefotaxime into a reactive, silylated derivative of formula VII, whereby R signifies hydrogen or a trialkylsilyl group. Suitable silylation agents are iodotrimethylsilane in the presence of a non-nucleophilic base, N,O-bis-(trimethylsilyl)-trifluoroacetamide (BSTFA), (for example U.S. Pat. No. 4,336,253); N-methyl-N-trimethyl-silyltrifluoroacetamide (MSTFA) (for example EP 74 268); 1,1,1,3,3,3-hexamethyldisilazane (HMDS) or a combination of all the said silylation agents. The compound of formula VIII is then produced in known manner with iodotrimethylsilane.

According to the above synthesis method, the silylated compound of formula VIII is treated simultaneously or substantially simultaneously with a protic solvent and N-methylpyrrolidone, whereby in a first step the compound of formula IX is produced and this is then rapidly reacted with N-methylpyrrolidine. The reaction accordingly illustrates a desilylation reaction, followed by salt formation on the carboxylic acid and nucleophilic substitution. This principle simultaneously minimises the instability of the highly reactive iodomethyl grouping by an in situ reaction with N-methylpyrrolidine, and through the (desilylation) salt formation on the carboxylic acid, by-product Δ2 formation is drastically reduced.

Suitable protic solvents are, in particular, alcohols, for example $C_1$-$C_4$-alcohols, preferred alcohols being ethanol and isopropanol. The amount of protic solvent is not critical, however the applicants have obtained favourable results when the reaction proceeds in a homogeneous solution or suspension, and through insolubility, the compound of formula IX is extracted from the possible further reaction in salt form or in free acid form.

In a preferred embodiment, the compound of formula VIII is mixed with a mixture of N-methylpyrrolidine and alcohol, preferably isopropanol. In this way, not only does the above-described reaction sequence take place, but the title compound is obtained as an addition salt with hydroiodic acid. This can be isolated from the reaction mixture directly. The iodide is removed from the product simply by treatment in an aqueous or aqueous-organic solution, for example in a mixture of dichloromethane/water, with a commercial anion exchanger, for example with Amberlite LA-2 (from Rohm & Haas), and by adding hydrochloric acid the active ingredient can subsequently be crystallised as the dihydrochloride hydrate according to known methods, for example from an aqueous/acetonic solution.

In one embodiment, the isolated hydroiodide may be converted into the corresponding free amphoteric ion (betaine) of formula XI, for example by treatment with a trialkylamine, e.g. trimethylamine, triethylamine or tributylamine, in an organic solvent such as dichloromethane, and after isolation by known methods, this may can be converted into the title compound cefepime dihydrochloride hydrate.

XI

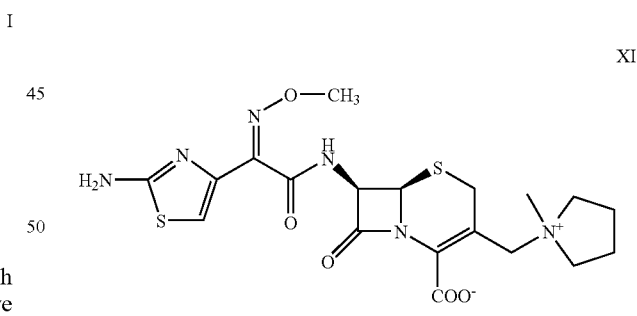

A further aspect of this invention provides a novel process for the production of cefepime which is notable for the simplicity of the choice of solvent and the accessibility and facile handling of the 7-acyl side chain, and which at the same time leads to an active ingredient with high purity in respect of the above-mentioned by-products.

The process comprises the reaction of a pyrrolidinium-1-[(7-amino-2-carboxy-8-oxo-5-thia-1-azabicyclo[4.2.0]oct-2-en-yl)methyl]-halide, an acid addition salt thereof or its free base of formula IIA with (Z)-(2-aminothiazol-4-yl)methoxy-imino-acetic acid-2-mercaptobenzotiazolylester of formula XII

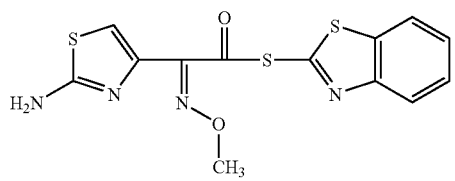

in an acetonic or aqueous/acetonic solution, optionally in the presence of a base, wherein cefepime dihydrochloride monohydrate is precipitated in crystalline form directly from the reaction mixture by adding HCl.

The process is straightforward. Neither extraction steps nor more complex purification operations are necessary. The solvent regeneration is an especially simple procedure, in that only one solvent is used both for the acylation reaction and for the crystallisation step. The intermediate compound of formula IIA may be present as mono-addition salt or di-addition salt or a mixture thereof In addition, the intermediate of formula IIA may be present in the form of a solvate, for example a hydrate. The usual addition salts are represented by the mono- and dihydrochloride or the hydriodide.

Depending on the salt form, the corresponding acid addition salt is released for the reaction with the acylation agent with the assistance of the necessary amount of a base, preferably a trialkylamine. Accordingly, a mono-addition salt is released with approximately one molar equivalent of base, and a di-addition salt is correspondingly released with approximately two. However, it is also possible to react the corresponding acid addition salt with (Z)-(2-aminothiazol-4-yl)methoxyimino-acetic acid-2-mercapto-benzothiazolylester without adding a base.

If the intermediate of formula IIA is used as the mono- or dihydrochloride, the active ingredient cefepime is obtained as the pure dihydrochloride. If the intermediate is used as the hydriodide, the recrystallised product is practically and substantially free from traces of iodide.

Alternatively, foreign ions can be removed from the reaction solutions by known methods, for example with the assistance of an anion exchanger.

Suitable trialkylamines are $C_1$-$C_8$-trialkylamines, for example triethylamine or tributylamine. The presence of water in the acylation reaction in principle also allows the use of inorganic bases, for example sodium or potassium hydroxide or an alkali hydrogen carbonate or alkali carbonate, e.g. sodium or potassium hydrogen carbonate or carbonate.

The reaction is preferably carried out in the presence of water: the amount of water is not critical; there must be balanced solubility of the cephalosporin intermediate of formula IIA and of the active ester of formula XII. The water/acetone ratio may be between 1:10 to 10:1, and preferably a water/acetone ratio of 1:1 to 1:5 is used for the acylation reaction. After the acylation reaction, in order to crystallise cefepime dihydrochloride, hydrochloric acid is added, preferably aqueous concentrated hydrochloric acid, and a pH value of less than 3, preferably less than 1, is set. By adding acetone, the crystallisation of cefepime dihydrochloride is then completed. Preferred water/acetone ratios in the crystallisation step are ratios of 1:1 to 1:20, especially ratios of 1:3 to 1:10.

The processes of this invention may be carried out between −40° C. and room temperature, for example between −35° C. and 15° C., preferably between −25° C. and about 1° C.

Following is a description by way of example only of processes of this invention.

Figure 1:
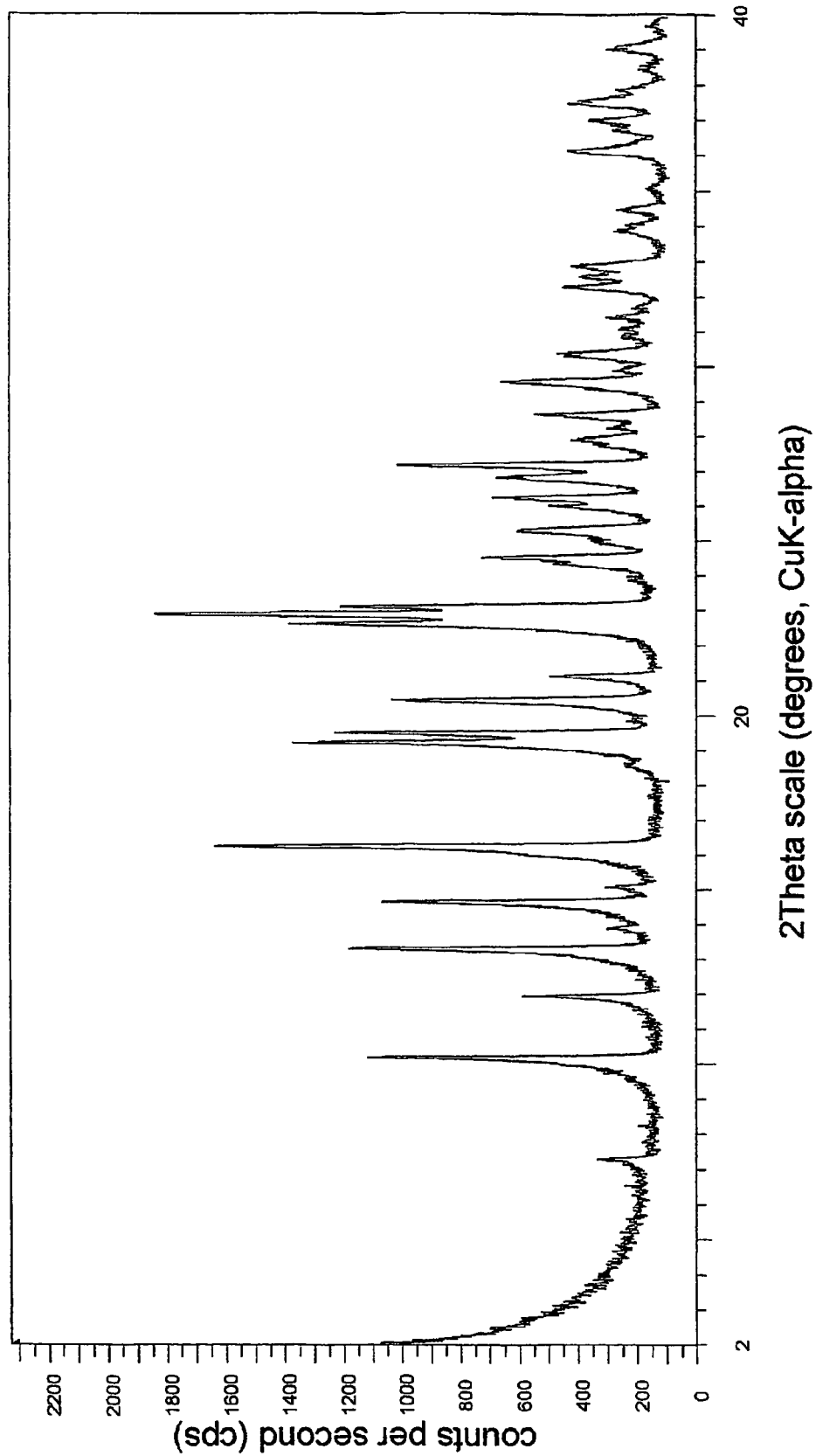
FIG. 1 is an X-ray spectrum of the compound of formula V as hydrochloride.

The following abbreviations are used:
NMP$^+$ to denote N-methylpyrrolidinium
NMP-ACA to denote an intermediate compound of Formula IIA

EXAMPLE 1

Preparation of Starting Material
4chloro-2-methoxyimino-3-oxo-butyryl chloride

A solution of 0.488 g of 4-chloro-2-methoxyiminobutyric acid in 8.0 ml of acetonitrile is mixed at −20° C. with 0.353 g of chloromethylene iminium chloride (Vilsmeier reagent) and stirred for 1 hour at −20° C.

EXAMPLE 2a

Preparation of 1-[[(6R,7R)-7-[[(2Z)-(4-chloro-2-methoxyimino-3-oxo-butyryl]amino]-2-carboxy-8-oxo-5-thia-1-azabicyclo[4.2.0]oct-2-en-3-yl]methyl]-1-methyl-pyrrolidinium hydrochloride 1.55 g of N,O-bistrimethylsilyacetamide are added dropwise at room temperature to a suspension of 0.835 g of NMP-ACA.2HCl in 10.5 ml of acetonitrile. After stirring for 25 mins at room temperature, the solution obtained is cooled to −35° C. At this temperature, a solution of 4-chloro-2-methoxyimino-3-oxo-butyryl chloride in acetonitrile (for preparation see example 1a), which has been cooled to −20° C., is added. After stirring for 1 hour in a cooling bath at −35° C., 2 ml of isopropanol are added dropwise. The resulting suspension is heated to 0° C. and stirred for 1 hour in an ice bath. The suspension is then filtered. The filter cake is washed with acetonitrile. After drying in a vacuum at room temperature, 1.42 g of product is obtained as a white crystalline powder.

$^1$H-NMR spectrum (DMSO-d6, δ in ppm) 1.957-1.690 (m, 2H, pyrrolidinyl-H); 2.943 (s, 3H, N—CH3); 3.371-3.701 (m, 5H, pyrrolidinyl-H, S—CH2); 3.866 (1H, J=10.0 Hz, S—CH2); 4.060 (s, 3H, OCH3); 4.329 and 4.597 (ABq, 2H, J=13.7 Hz,. —CH2-N); 4.846 (s, 2H, CH2Cl); 5.322 (d, 1H, 5.1 Hz, H6); 5.884 (dd, 1H, J=8.4 Hz, J=5.1 Hz, H7); 9.555 (d, 1H, NH)

EXAMPLE 2b

Preparation of 1-[[(6R,7R)-7-[[(2Z)-(4-chloro-2-methoxyimino-3-oxo-butyryl]amino]-2-carboxy-8-oxo-5-thia-1-azabicyclo[4.2.0]oct-2-en-3-yl]methyl]-1-methyl-pyrrolidinium hydrochloride 1.63 g of trimethylsilychloride are added dropwise at room temperature to a suspension of 5.00 g of NMP-ACA.HCl in 190 ml of acetonitrile. After stirring for 10 mins at room temperature 8.5 ml acetontrile are added and then the suspension is cooled to 0° C. At this temperature 7.74 g N,O-bistrimethylsilyacetamide are added dropwise. After stirring for 20 mins the resulting solution is cooled to −20° C. At this temperature a solution of 4-chloro-2-methoxyimino-3-oxo-butyryl chloride in acetonitrile (prepared from 3.03 g 4-chloro-2-methoxyimino-3-oxo-butyryl acid, 2.16 g of chloromethylene iminium chloride (Vilsmeier reagent) and 45 ml acetonitrile; preparation see example 1a), which has been cooled to −20° C., is added. After stirring for 1 hour in a cooling bath at −25° C. the cold reaction mixture is added within 20 minutes to a mixture of 148 ml acetontrile and 14 ml methanol and by addition of a solution of ethyldiisopropylamine in acetonitrile (10%) the pH is maintained in the range 2.0-1.5. The resulting suspension is stirred for 1 hour in an ice bath. The suspension is then filtered. The filter cake is washed with acetonitrile. After drying in a vacuum at room temperature, 7.20 g of product is obtained as a white crystalline powder.

The corresponding X-ray spectrum is shown in FIG. 1.

EXAMPLE 2c

Preparation of 1-[[(6R,7R)-7-[[(2Z)-(4chloro-2-methoxyimino-3-oxo-butyryl]amino]-2-carboxy-8-oxo-5-thia-1-azabicyclo[4.2.0]oct-2-en-3-yl]methyl]-1-methyl-pyrrolidinium inner salt 10.64 g of (4-chloro-2-methoxyimino-3-oxo-butyryl]amino]-2-carboxy-8-oxo-5-thia-1-azabicyclo[4.2.0]oct-2-en-3-yl]methyl]-1-methyl-pyrrolidinium hydrochloride (for preparation see above) is suspended in 95 ml cold methanol. To the suspension is added dropwise at 0° C. a solution of 8.1 g triethylamine in 30 ml methanol. The suspension is stirred for 1 hour in an ice bath. The suspension is then filtered. The filter cake is washed with cold methanol. After drying in a vacuum at room temperature, 7.57 g of product is obtained as a white crystalline powder.

Figure 2:
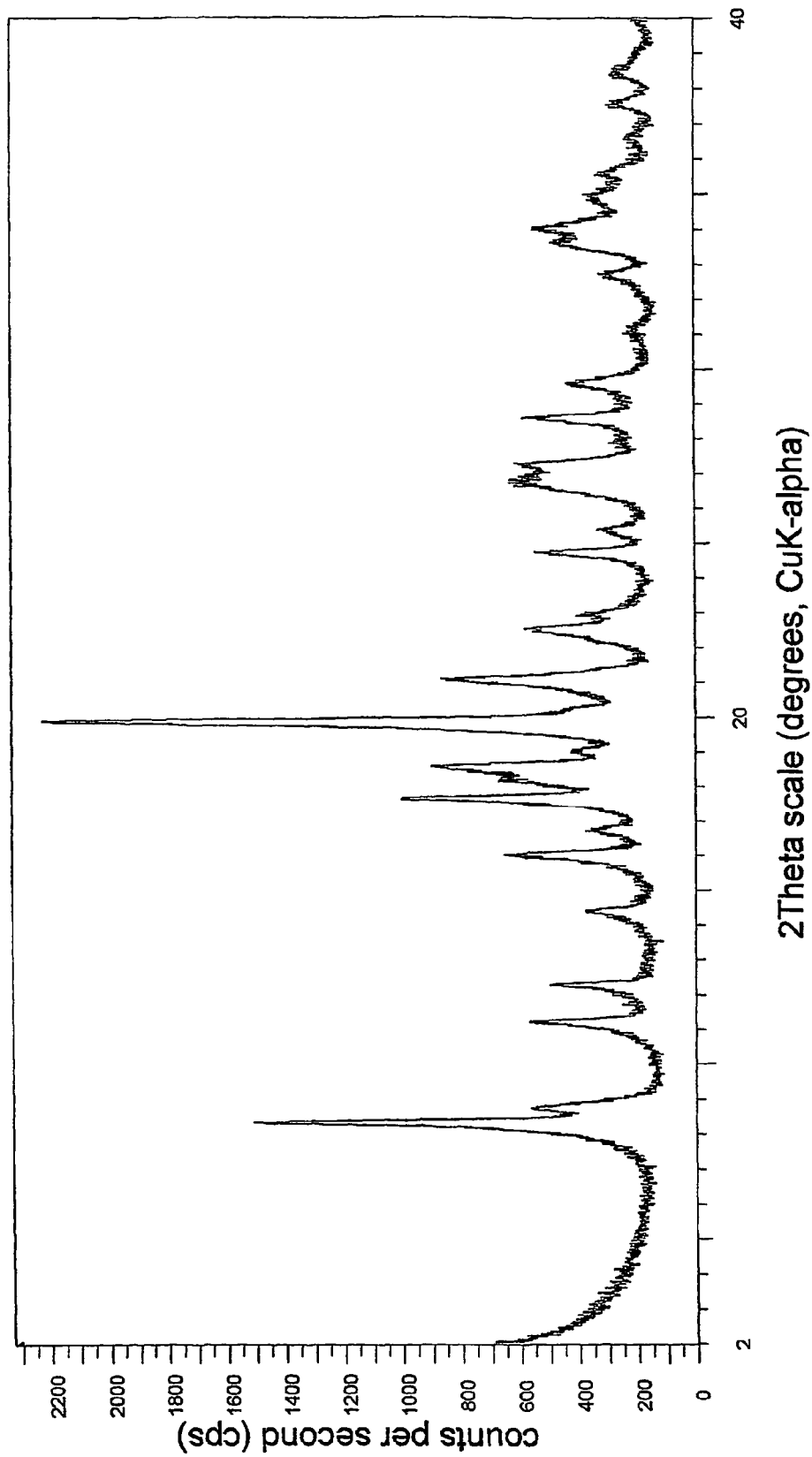
FIG. 2 is an X-ray spectrum of the compound of formula V as base (betaine).

The corresponding X-ray spectrum is shown in FIG. 2.

EXAMPLE 3

Preparation of 1-[[(6R,7R)-7-[[(2Z)-(2-amino-4-thiazolyl)methoxyimino)acetyl]amino]-2-carboxy-8-oxo-5-thia-1-azabicyclo[4.2.0]oct-2-en-3-yl]methyl]-1-methyl-pyrrolidinium dihydrochloride hydrate (cefepime dihydrochloride monohydrate)

0.990 g of 1-[[(6R,7R)-7-[[(2Z)-(4-chloro-2-methoxyimino-3-oxo-butyryl]amino]-2-carboxy-8-oxo -5-thia-1-azabicyclo[4.2.0]oct-2-en-3-yl]methyl]-1-methyl-pyrrolidinium hydrochloride are added at 4° C. to a solution of 0.152 g of thiourea in 5 ml of H$_2$O. The pH of the suspension is adjusted to pH 6.0 with ion exchanger LA-2 and maintained in the pH range of 5.5 to 6.0 by adding LA-2 dropwise. After stirring for 8.5 hours at 2 to 4° C., the reaction mixture is washed with 10 ml of methylene chloride. After phase separation, the aqueous phase is washed a second time with 10 ml of methylene chloride. The organic phases are combined and then extracted with 3 ml of H$_2$O. The aqueous phases are combined and mixed with 0.20 g of activated carbon. After stirring for 10 minutes, the carbon suspension is filtered. The carbon cake is washed with 1.5 ml of H$_2$O. The filtrate and washing water are combined, acidified with 6 m HCl to pH 0.6 and mixed with 50 ml of acetone. After adding seed crystals, stirring is effected for 15 minutes at room temperature, and then a further 50 ml of acetone is added dropwise over the course of 1 hour. The crystal suspension obtained is cooled to 0° C. After stirring for 1 hour in an ice bath, the suspension is filtered and the filter cake is washed with acetone. After drying in a vacuum at room temperature, 0.561 g of the title compound are obtained in the form of a white crystalline powder.

HPLC purity: 99.6 area %

EXAMPLE 4

Preparation of 1-[[(6R,7R)-7-[[(2Z)-(2-amino-4thiazolyl)methoxyimino)acetyl]amino]-2-carboxy-8-oxo-5-thia-1-azabicyclo[4.2.0]oct-2-en-3-yl]methyl]-1-methyl-pyrrolidinium dihydrochloride hydrate (cefepime dihydrochloride monohydrate)

1.55 g of N,O-bistrimethylsilylacetamide are added dropwise at 1° C. to a suspension of 0.835 g of pyrrolidinium-1-[(7-amino-2-carboxy-8-oxo-5-thia-1-azabicyclo[4.2.0]oct-2-en-yl)methyl]-dihydrochloride in 10.5 ml of acetonitrile. After stirring for 45 mins in an ice bath, the solution obtained is cooled to −35° C. At this temperature, a solution of 4-chloro-2-methoxyimino-3-oxo-butyryl chloride (for preparation see example 1a), which has been cooled to −20° C., is added. After stirring for 1 hour in a cooling bath at −35° C., 2 ml of H$_2$O are added dropwise. After stirring for 10 minutes at −35° C., 0.38 g of thiourea are added. The reaction mixture is subsequently heated to 0° C. and the pH is adjusted to 6.0 by adding ion exchanger LA-2, and is maintained at this pH. After stirring for 2 hours in an ice bath, the 2-phase reaction mixture obtained is mixed with 2 ml of H$_2$O. After stirring for a further 16 hours at 0 to 4° C., the pH is acidified to pH 0.6 with 6 m HCl. After adding 50 ml of methylene chloride, the phases are separated. The methylene chloride phase is then extracted with 3 ml of H$_2$O. The aqueous phases are combined and mixed with 0.10 g of activated carbon. After stirring for 10 minutes, the activated carbon suspension is filtered. The carbon cake is washed with 1 ml of H$_2$O. The filtrate and washing water are combined and diluted with 30 ml of acetone. After adding seed crystals, stirring is effected for 30 minutes at room temperature. Then, 20 ml of acetone are added dropwise to the resulting crystal suspension over the course of 30 minutes. The suspension is cooled to 0° C. After stirring for 1 hour in an ice bath, the product is isolated and the filter cake is washed with acetone. After drying in a vacuum at room temperature, 0.742 g of the title compound are obtained in the form of a white crystalline powder.

HPLC purity: 99.5 area %

EXAMPLE 5

Preparation of 1-[[(6R,7R)-7-[[(2Z)-(2-amino-4-thiazolyl)methoxyimino)acetyl]amino]-2-carboxy-8-oxo-5-thia-1-azabicyclo[4.2.0]oct-2-en-3-yl]methyl]-1-methyl-pyrrolidinium dihydrochloride hydrate (cefepime dihydrochloride monohydrate)

1.706 g of pyrrolidinium-1-[(7-amino-2-carboxy-8-oxo-5-thia-1-azabicyclo[4.2.0]oct-2-en-yl)methyl]-dihydrochloride are added to a mixture of 10 ml of H$_2$O and 5 ml of methylene chloride, and the pH is adjusted to 6.50 by adding ion exchanger LA-2. The 2-phase mixture is cooled in an ice bath to 1° C. At this temperature, a solution of 4-chloro-2-methoxyimino-3-oxo-butyryl chloride, produced from 1.464 g of 4-chloro-2-methoxyimino-3-oxo-butyric acid (see example 1a), which has been cooled to −20° C., is added dropwise over the course of 1 hour, whereby the pH is maintained in the range of 6.0 to 6.5 by adding base LA-2. After stirring for 15 minutes in an ice bath, 0.76 g of thiourea are added and stirring is effected for 16 hours at 2-4° C. The pH is maintained in the range of 5.5 to 6.0 with LA-2. The reaction mixture is subsequently diluted with 100 ml of methylene chloride. After phase separation, the aqueous phase is washed with 50 ml of methylene chloride. The methylene chloride phases are combined and then extracted with 3 ml of $H_2O$. The product-containing aqueous phases are combined and mixed with 0.20 g of activated carbon. After stirring for 10 minutes, the activated carbon suspension is filtered. The carbon cake is washed with 1.5 ml of $H_2O$. The filtrate and washing water are combined and diluted with 60 ml of acetone. After adding seed crystals, stirring is effected for 30 minutes at room temperature. Then, 40 ml of acetone are added dropwise to the resulting crystal suspension over the course of 30 minutes. The suspension is cooled to 0° C. After stirring for 1 hour in an ice bath, the product is isolated and the filter cake is washed with acetone. After drying in a vacuum at room temperature, 1.236 g of the title compound are obtained in the form of a white crystalline powder.

HPLC purity: 90.0 area %

EXAMPLE 6

Preparation of 1-[[(6R,7R)-7-[[(2Z)-(2-amino-4-thiazolyl)methoxyimino)acetyl]amino]-2-carboxy-8-oxo-5-thia-1-azabicyclo[4.2.0]oct-2-en-3-yl]methyl]-1-methyl-pyrrolidinium hydriodide 100.0 g of cefotaxime are suspended in 1.2 l of methylene chloride and heated to reflux temperature. Whilst boiling under reflux, 2.5 ml of hexamethyldisilazane (HMDS) and 0.2 ml of trimethyliodosilane are added. Then, 102 ml of HMDS are added dropwise whilst stirring, and stirring is effected at this temperature for 1 hour, whereby the resulting ammonia is removed by passing nitrogen into the reaction suspension. Then, the clear solution obtained is cooled to 10° C. 70 ml of trimethyliodosilane are added dropwise at this temperature. After stirring for 60 minutes, 10 ml of trimethyliodosilane are added dropwise, and after a further 30 minutes, a further 15 ml of trimethyliodosilane are added. After stirring for 165 minutes at 10° C., the reaction solution is stirred over the course of 2 minutes into a solution of 350 ml of N-methylpyrrolidine in 9 l of isopropanol, which has a temperature of 18° C. The resulting suspension is stirred for 1 hour at room temperature. Then, it is filtered through a glass sintering filter and the filter cake is washed with 500 ml of isopropanol. After drying in a vacuum at room temperature, 97.7 g of the title compound are obtained in the form of a yellow coloured powder.

EXAMPLE 7

Preparation of 1-[[(6R,7R)-7-[[(2Z)-(2-amino4-thiazolyl)methoxyimino)acetyl]amino]-2-carboxy-8-oxo-5-thia-1-azabicyclo[4.2.0]oct-2-en-3-yl]methyl]-1-methyl-pyrrolidinium dihydrochloride hydrate 4.00 g of 1-[[(6R,7R)-7-[[(2Z)-(2-amino-4-thiazolyl)methoxyimino)acetyl]amino]-2-carboxy-8-oxo -5-thia-1-azabicyclo[4.2.0]oct-2-en-3-yl]methyl]-1-methyl-pyrrolidinium hydriodide are dissolved at room temperature in a mixture of 10 ml of $H_2O$ and 30 ml of methylene chloride. The pH of the mixture is adjusted to 7.3 through the dropwise addition of ion exchanger LA-2. After stirring for 15 minutes, the phases are separated. The aqueous phase is adjusted to pH 2.5 with conc. hydrochloric acid and stirred for 15 minutes. Then, the precipitate formed is separated by filtration. The clear filtrate is acidified to pH 1.0 with conc. hydrochloric acid and mixed with 1.6 g of activated carbon. After stirring for 10 minutes, the activated carbon is removed by filtration and the carbon cake is washed with 5 ml of $H_2O$. The filtrate and washing water are combined, acidified to pH 0.5 with conc. hydrochloric acid and diluted with 50 ml of acetone. Seed crystals are added, and the resulting crystal suspension is stirred for ca. 20 minutes at room temperature. Subsequently, a further 50 ml of acetone is added dropwise over the course of 30 minutes. When the acetone addition is complete, the crystal suspension is cooled to 0° C. After stirring for 1 hour in an ice bath, the suspension is filtered and the filter cake is washed with acetone. After drying in a vacuum at room temperature, 0.85g of the title compound are obtained in the form of a white crystalline powder. Yield: 36.8%.

HPLC purity: >99 area %

EXAMPLE 8

Preparation of 1-[[(6R,7R)-7-[[(2Z)-(2-amino-4thiazolyl)methoxyimino)acetyl]amino]-2-carboxy-8-oxo-5-thia-1 azabicyclo[4.2.0]oct-2-en-3-yl]methyl]-1-methyl-pyrrolidinium dihydrochloride hydrate 44.3 g of pyrrolidinium-1-[(7-amino-2-carboxy-8-oxo-5-thia-1-azabicyclo[4.2.0]oct-2-en-yl)methyl]-iodide monohydrate (NMP-ACA) are suspended in a mixture of 200 ml of $H_2O$ and 400 ml of acetone. 38.5 g of (Z)-(2-aminothiazol-4-yl)methoxy-iminoacetic acid-2-mercaptobenzothiazolylester are added to the suspension. At a temperature of ca. 15°, a mixture of 13.9 ml of triethylamine and 14 ml of acetone is slowly added dropwise to the suspension over the course of 3 hours. The resulting cloudy solution is stirred for a total of 6.5 hours at 20° C.

33 ml of 37% HCl are subsequently added to the reaction mixture, and then ca. 300 ml of 15 acetone are added whilst stirring. The mixture is seeded with seed crystals, and within ca. 90 minutes a suspension is produced. Subsequently, within 90 minutes, 1700 ml of acetone are added dropwise whilst stirring gently. The suspension is stirred for a further one hour at room temperature, and then the title compound is isolated through a suction filter, and the product is washed with 250 ml of acetone/$H_2O$ mixture (90/10) and with a total of 500 ml of acetone in two portions. The product is subsequently dried for ca. 18 hours at room temperature in a vacuum drying chamber.

Yield 51.8 g purity: HPLC: 98.8 area percent

EXAMPLE 9

Recrystallisation of 1-[[(6R,7R)-7-[[(2Z)-(2-amino-4-thiazolyl)methoxyimino)acetyl]amino]-2-carboxy-8-oxo-5-thia-1-azabicyclo[4.2.0]oct-2-en-3-yl]methyl]-1-methyl-pyrrolidinium dihydrochloride hydrate 50.0 g of cefepime dihydrochloride hydrate are dissolved in 200 ml of $H_2O$. 22 ml of 6 n HCl are added and then the solution is mixed with 5 g of activated carbon. The suspension is stirred for 10 minutes at room temperature and then filtered through a suction filter. The filter layer is then washed with 50 ml of $H_2O$, and the combined filtrates are mixed with 600 ml of acetone until turbidity occurs. The resulting suspension is stirred for 15 minutes and then a further 1400 ml of acetone are added over the course of one hour whilst stirring gently. The suspension is stirred for another one hour at room temperature, and the product is subsequently isolated through a suction filter. The product is washed with a total of 500 ml of acetone and dried for ca. 18 hours at room temperature in a vacuum drying chamber.

Yield 45.01 g purity HPLC: 99.7 area percent

X-ray Diffraction Measurements for Examples 2b and 2c

Equipment used:
X-Ray Powder Diffractometer D-8 (AXS-BRUKER)
theta-theta-goniometer, sample changer
target: Copper, $K\alpha1+K\alpha2\lambda=1.5406$ Å
parallel beam optics (receiving soller-slit: 0.07 mm)
Scintillation counter, standard sample holders
Data collection parameters: 40 kV, 40 mA, 2-40° θ/2θ, 0.01 steps, 2 seconds

The invention claimed is:

1. A process for producing a compound of formula I

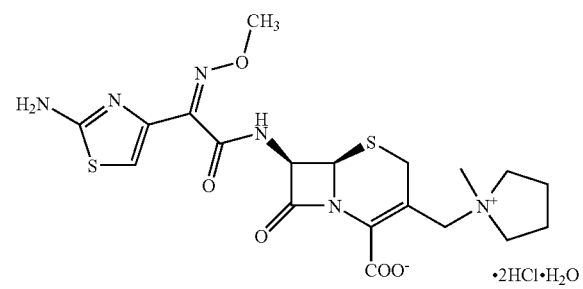

wherein a compound of formula IIA, or a hydrate of a compound of formula IIA,

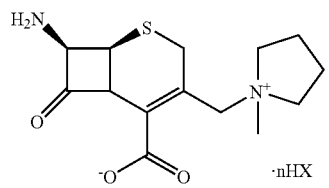

wherein n is 1 or 2 and X signifies chloride, bromide or iodide, is reacted with a reactive derivative of formula III

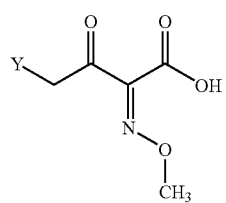

wherein Y signifies halogen, to form a compound of formula V

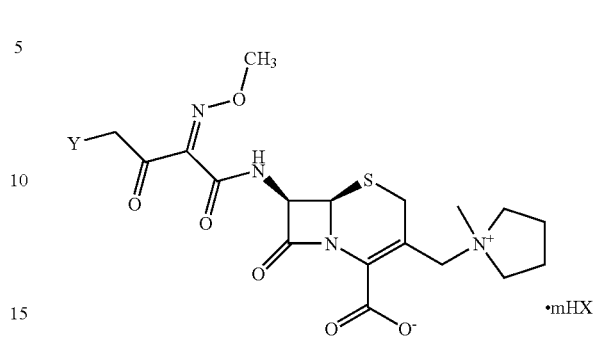

wherein m is 1 and wherein optionally the compound of formula V is isolated, wherein the compound of formula V is cyclised with thiourea in an aqueous or organic-aqueous medium, wherein optionally salt that is present is then removed, and wherein the compound of formula I is subsequently isolated from aqueous acetonic solution after addition of hydrochloric acid.

2. A process for producing a compound of formula I

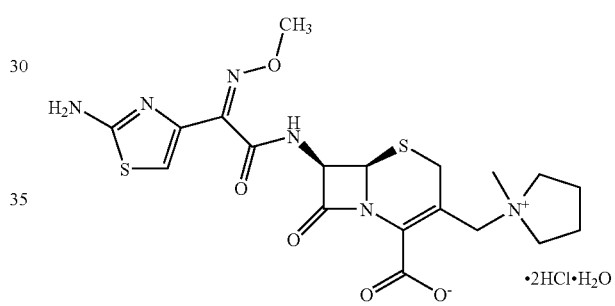

wherein a compound of formula IIB

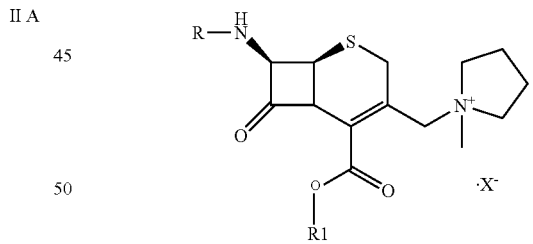

wherein
R₁ is a trialkylsilyl group,
R is hydrogen or a trialkylsilyl group, and
X signifies chloride, bromide or iodide is reacted with a reactive derivative of formula III

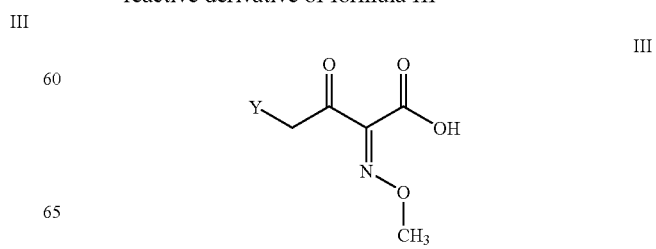

wherein Y signifies halogen, to form a compound of formula IV

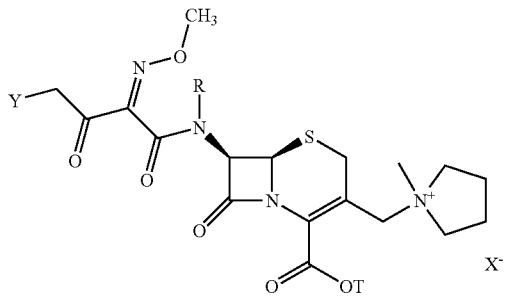

IV wherein T is trialkylsilyl, the silyl protecting group is removed to form a compound of the formula V, wherein m is 1,

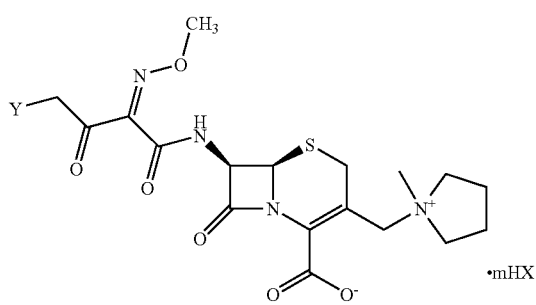

V wherein optionally the compound of formula V is isolated, and wherein the compound of formula V is cyclized with thiourea in an aqueous or organic-aqueous medium and wherein optionally salt that is present is then removed, and wherein the compound of formula I is subsequently isolated from aqueous acetonic solution after addition of hydrochloric acid.

3. A process as claimed in claim 1, wherein pyrrolidinium-1-[(7-amino-2-carboxy-8-oxo-5-thia-1-azabicyclo[4.2.0]oct-2-en-yl) methyl]-iodide monohydrate is used.

4. A process as claimed in claim 1, wherein pyrrolidinium-1-[(7-amino-2-carboxy-8-oxo-5-thia-1-azabicyclo[4.2.0]oct-2-en-yl) methyl]-chloride or pyrrolidinium-1-[(7-amino-2-carboxylato-8-oxo-5-thia-1-azabicyclo [4.2.0]oct-2-en-yl) methyl]dihydrochloride is used, optionally in hydrated form.

5. A compound of formula V

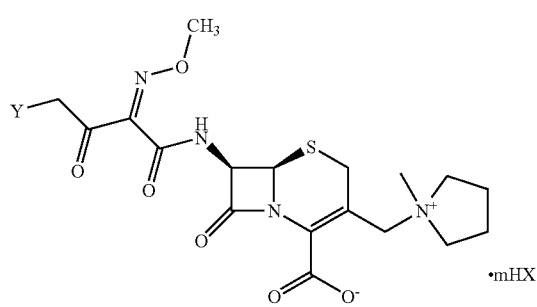

V wherein Y and X are Cl and wherein m=1.

6. A compound as claimed in claim 5 having an X-ray powder diffraction pattern substantially as that shown in FIG. 1.

7. A process according to claim 1, wherein 4-chloro-2-methoxyimino-3-oxo-butyryl chloride is used as the reactive derivative of formula III.

* * * * *

UNITED STATES PATENT AND TRADEMARK OFFICE
CERTIFICATE OF CORRECTION

| | | |
|---|---|---|
| PATENT NO. | : 7,847,093 B2 | Page 1 of 1 |
| APPLICATION NO. | : 10/552858 | |
| DATED | : December 7, 2010 | |
| INVENTOR(S) | : Johannes Ludescher et al. | |

It is certified that error appears in the above-identified patent and that said Letters Patent is hereby corrected as shown below:

In the Specification:

Column 1, line 7, after "OF", delete "CEFEPI" and insert therefor -- CEFEPIME --.

Column 1, line 24, at the end of the second paragraph, after "formula I," please insert -- . --.

Column 4, line 11, after "of" (second occurrence), delete "formula I" and insert therefor -- formula II --.

Column 7, line 22, after "thereof", and before "In Addition," add -- . --.

Column 7, line 41, at the beginning of the paragraph, delete "Altermatively" and insert therefor -- Alternatively --.

Column 12, line 30, after "ca," delete "15°," and insert therefor -- 15°C --.

Column 12, line 62, after "6," delete lower case "n," and insert therefor -- N --.

Column 15, Claim 2, line 39, after "is," please delete "cyclized" and insert therefor -- cyclised --.

Signed and Sealed this

Twenty-third Day of August, 2011

David J. Kappos
*Director of the United States Patent and Trademark Office*